United States Patent
Iftime et al.

(10) Patent No.: US 11,124,790 B2
(45) Date of Patent: Sep. 21, 2021

(54) CATALYST FOR HIGH THROUGHPUT ENZYMATIC CATALYSIS

(71) Applicant: PALO ALTO RESEARCH CENTER INCORPORATED, Palo Alto, CA (US)

(72) Inventors: Gabriel Iftime, Dublin, CA (US); Eric Cocker, Redwood City, CA (US); Sean Garner, Redwood City, CA (US); Jessica Louis Baker Rivest, Palo Alto, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 156 days.

(21) Appl. No.: 16/126,226

(22) Filed: Sep. 10, 2018

(65) Prior Publication Data
US 2019/0241883 A1 Aug. 8, 2019

Related U.S. Application Data

(60) Provisional application No. 62/628,010, filed on Feb. 8, 2018.

(51) Int. Cl.
*C12N 11/14* (2006.01)
*C12P 7/04* (2006.01)
(Continued)

(52) U.S. Cl.
CPC ............. *C12N 11/14* (2013.01); *C12P 7/04* (2013.01); *C25B 3/23* (2021.01); *C25B 11/031* (2021.01);
(Continued)

(58) Field of Classification Search
CPC .... B22F 2998/00; B22F 1/0048; B22F 9/026; B22F 9/30; A61B 2562/028; A61B 5/14532; A61B 5/14546; A61B 5/1473; A61B 5/14865; A61B 5/6848; B01J 21/18; B01J 23/00; B01J 23/34; B01J 23/40; B01J 31/06; B01J 35/002; B01J 35/0026; B01J 35/0033; B01J 35/023; B01J 35/08; B01J 37/0054; B01J 37/343; B01J 19/0046; B01J 2219/00283; B01J 2219/00295; B01J 2219/00299; B01J 2219/00308; B01J 2219/00333; B01J 2219/00344; B01J 2219/00461; B01J 2219/00463; B01J 2219/005; B01J 2219/00502; B01J 2219/0054; B01J 2219/00542; B01J 2219/00547; B01J 2219/00549; B01J 2219/00551; B01J 2219/00554; B01J 2219/0056; B01J 2219/00563; B01J 2219/00567; B01J 2219/00569; B01J 2219/00585; B01J 2219/0059; B01J 2219/00592; B01J 2219/00596; B01J 2219/00689; B01J 2219/00695; B01J 2219/0072; B01J 2219/00722; B01J 2219/00725; B01J 20/0229; B01J 20/0248; B01J 20/103; B01J 20/28004; B01J 20/283; B01J 20/286; B01J 20/3085; B01J 20/3092; B01J 20/3204; B01J 20/3236; B01J 20/3246; B01J 2219/0031; B01J 2219/00313; B01J 2219/00319; B01J 2219/00454; B01J 2219/00691; B01J 2220/54; B01J 2220/56; B01J 2220/58; B01J 31/003; B82Y 30/00; B82Y 10/00; C09D 11/101; C09D 11/30; C22C 29/00; C22C 32/0084; C23C 18/06; C23C 18/08; H01B 1/026; H01L 21/288; H01L 21/31691; H01M 12/08; H01M 2008/1095; H01M 4/8605; H01M 4/8636; H01M 4/881; H01M 4/8828; H01M 4/8832; H01M 4/8842; H01M 4/8882; H01M 4/90; H01M 4/9016; H01M 4/9083; H01M 4/92;
(Continued)

(56) References Cited

U.S. PATENT DOCUMENTS 4,115,198 A * 9/1978 Coughlin ............... A61K 9/143
435/176
4,648,975 A * 3/1987 Barkatt .................. B01J 20/283
210/198.2

(Continued)

OTHER PUBLICATIONS

Wikipedia Electrocatalyst, https://en.wikipedia.org/wiki/Electrocatalyst, pp. 1-4. (Year: 2020).*
(Continued)

*Primary Examiner* — Deborah K Ware
(74) *Attorney, Agent, or Firm* — Miller Nash LLP

(57) ABSTRACT

A catalyst having a porous support having at least one of thermally or electrically conductive particles bonded by a polymer, and enzymes embedded into pores of the porous support. A process of manufacturing an enzyme-embedded porous support includes forming solution of monomers, enzymes, a solvent, and at least one of electrically and thermally conductive particles, polymerizing the monomers by adding initiators to the solution, and evaporating the solvent to produce an enzyme-embedded porous support. A process of manufacturing an enzyme embedded porous support, includes mixing enzymes, at least one of electrically conductive or thermally conductive particles, and a polymer in a solvent, and evaporating the solvent.

20 Claims, 2 Drawing Sheets

(51) Int. Cl.
  *C25B 11/04* (2021.01)
  *C25B 3/23* (2021.01)
  *C25B 11/031* (2021.01)
  *C25B 11/051* (2021.01)
  *C25B 11/075* (2021.01)

(52) U.S. Cl.
  CPC ............ *C25B 11/04* (2013.01); *C25B 11/051* (2021.01); *C25B 11/075* (2021.01)

(58) Field of Classification Search
  CPC .... H01M 4/926; H01M 4/96; H01M 8/04197; H01M 8/1004; H01M 8/1009; H01M 10/4235; H01M 4/134; H01M 4/382; H01M 4/405; H01M 10/0525; H01M 10/0567; H01M 10/0569; H01M 10/44; H01M 2004/021; H01M 4/136; H01M 4/366; H01M 10/045; H01M 10/42; H01M 2010/4292; H01M 2/1673; H01M 4/5815; H05K 1/0346; H05K 1/095; H05K 1/097; H05K 1/162; H05K 2203/013; H05K 2203/1142; H05K 3/105; H05K 3/125; H05K 7/20836; Y02E 60/128; Y02E 60/523; Y02P 70/56; Y02P 20/59; Y02P 20/588; F01K 13/006; F22B 1/00; G06F 1/206; H02J 9/00; H04L 63/20; Y02D 10/16; Y10T 307/615; C12N 11/04; C12N 11/08; C12N 11/14; C12N 9/88; C12N 9/96; C12P 7/04; C12P 7/625; C12P 19/02; C12P 19/14; C12P 19/20; C25B 11/035; C25B 11/04; C25B 11/0405; C25B 11/0447; C25B 3/02; C25B 11/031; C25B 11/051; C25B 11/075; C25B 3/23; C07C 29/00; C07C 29/141; C07C 31/202; C07C 31/205; C07C 31/225; C07C 31/26; C07C 69/22; C07C 69/28; C07C 69/34; B01D 2257/504; B01D 53/1475; B01D 53/229; B01D 53/75; B01D 53/85; B01D 53/864; B01D 53/8671; Y02A 50/2359; Y02C 10/02; Y02C 10/04; Y02C 10/06; B01L 2300/0609; B01L 3/50825; B01L 2300/022; B01L 2400/0655; B01L 3/50255; B01L 3/5027; B01L 3/502761; B01L 3/5453; C07H 21/00; C07K 1/00; C07K 1/04; C07K 1/047; C08G 65/3322; C40B 40/06; C40B 40/10; C40B 60/14; C40B 70/00; C40B 50/14; G01N 2015/149; G01N 2035/00782; G01N 2333/9121; G01N 2500/00; G01N 35/00732; G01N 35/00871; G01N 33/542; G01N 33/54353; G01N 33/54393; G11C 13/0014; G11C 13/0019; G11C 13/025; G11C 2213/81; A61K 39/44; A61K 9/143; A61K 9/2009; C03C 11/005; C03C 1/002; C03C 23/0095; C07B 2200/09; C08J 2327/12; C08J 7/16; C13K 13/00; C13K 1/00; B33Y 80/00; C12M 21/18; C12M 23/24
  See application file for complete search history.

(56) References Cited

U.S. PATENT DOCUMENTS

| | | | | |
|---|---|---|---|---|
| 6,329,139 | B1* | 12/2001 | Nova | B01J 19/0046 209/597 |
| 6,340,588 | B1* | 1/2002 | Nova | B01J 19/0046 435/287.1 |
| 6,900,361 | B2* | 5/2005 | Elliott | C07C 29/00 435/105 |
| 7,098,163 | B2* | 8/2006 | Hampden-Smith | H01M 8/1004 502/101 |
| 7,642,213 | B2* | 1/2010 | Hampden-Smith | H01B 1/026 502/101 |
| 7,713,899 | B2* | 5/2010 | Hampden-Smith | C22C 32/0084 502/101 |
| 7,998,714 | B2* | 8/2011 | Gellett | B01D 53/8671 435/168 |
| 8,178,332 | B2* | 5/2012 | Gellett | B01D 53/85 435/174 |
| 8,560,039 | B2* | 10/2013 | Simpson | A61B 5/6848 600/347 |
| 9,284,583 | B2* | 3/2016 | Clendennen | C07C 69/22 |
| 9,339,222 | B2* | 5/2016 | Simpson | A61B 5/14865 |
| 9,543,787 | B2* | 1/2017 | Duchesneau | F22B 1/00 |
| 10,028,683 | B2* | 7/2018 | Simpson | A61B 5/1473 |
| 10,028,684 | B2* | 7/2018 | Simpson | A61B 5/1473 |
| 10,202,567 | B2* | 2/2019 | Stolaroff | C12N 11/04 |
| 10,561,352 | B2* | 2/2020 | Simpson | A61B 5/14546 |
| 10,629,947 | B2* | 4/2020 | Affinito | H01M 4/382 |
| 2004/0038808 | A1* | 2/2004 | Hampden-Smith | H01M 4/8636 502/180 |
| 2006/0269824 | A1* | 11/2006 | Hampden-Smith | H01M 4/96 502/101 |
| 2006/0292434 | A1* | 12/2006 | Hampden-Smith | H01M 4/96 429/480 |
| 2010/0076283 | A1* | 3/2010 | Simpson | A61B 5/14546 600/345 |
| 2010/0086983 | A1* | 4/2010 | Gellett | C12N 9/88 435/168 |
| 2011/0177398 | A1* | 7/2011 | Affinito | H01M 4/405 429/325 |
| 2011/0300623 | A1* | 12/2011 | Gellett | B01D 53/1475 435/289.1 |
| 2012/0070746 | A1* | 3/2012 | Mikhaylik | H01M 4/405 429/231.95 |
| 2012/0220025 | A1* | 8/2012 | Gellett | B01D 53/864 435/289.1 |
| 2013/0261417 | A1* | 10/2013 | Simpson | A61B 5/14546 600/345 |
| 2014/0183957 | A1* | 7/2014 | Duchesneau | F01K 13/006 307/64 |
| 2015/0010453 | A1* | 1/2015 | Gellett | B01D 53/229 423/230 |
| 2015/0025346 | A1* | 1/2015 | Simpson | A61B 5/14546 600/347 |
| 2016/0017385 | A1* | 1/2016 | Clendennen | C08G 65/3322 560/198 |
| 2016/0038065 | A1* | 2/2016 | Simpson | A61B 5/6848 600/347 |
| 2018/0008173 | A1* | 1/2018 | Simpson | A61B 5/14546 |
| 2018/0289294 | A1* | 10/2018 | Simpson | A61B 5/14865 |
| 2018/0317819 | A1* | 11/2018 | Simpson | A61B 5/14865 |
| 2020/0146595 | A1* | 5/2020 | Simpson | A61B 5/6848 |
| 2020/0220205 | A1* | 7/2020 | Affinito | H01M 10/0525 |

OTHER PUBLICATIONS

V.V. Vinogradov et al., "Enzyme renaturation to higher activity driven by sol-gel transition: Carbonic anhydrase," RCS Adv., 2015:5, 10862-10868.
E.A. Emam, "Gas Flaring in Industry: An Overview," Petroleum & Coal 57(5) 532, 2015.
A. Zaks et al., "Enzymatic Catalysis in Nonaqueous Solvents," J. Biol Chemistry, 263(7), pp. 3194-3201, 1988.
V. Stephankova et al., ACS Catal. 3, 2823, 2013.
S. Hermanova et al. Nanoscale, 7:5852, PJ Microbiol. Biotechnol (2016) 26(7), 1234.
K. Narsimhan et al., "Catalytic Oxidation of Methane into Methanol over Copper-Exchanged Zeolites with Oxygen at Low Temperature," ACS Cent. Sci. (2)424, 2015.

(56) References Cited

OTHER PUBLICATIONS

T.J. Lawton et al., "Methane-Oxidizing Enzymes: An Upstream Problem in Biological Gas-to-Liquids Conversion," J. Am. Chem. Soc., 138(3) pp. 9327-9340, 2016.
P. Mardina et al., Potential of Immobilized Whole-Cell Methylocella tundrae as a Biocatalyst for Methanol Production from Methane, J. Microbio. Biotechnol. 26(7), pp. 1234-1241, 2016.

* cited by examiner

CATALYST FOR HIGH THROUGHPUT ENZYMATIC CATALYSIS

RELATED APPLICATIONS

This application is a continuation of, and claims priority to, U.S. Provisional Patent Application No. 62/628,010, filed Feb. 8, 2018, which is incorporated herein by reference in its entirety.

TECHNICAL FIELD

This disclosure relates to gas-to-liquid (GTL) technology, more particularly to enzyme catalysis.

BACKGROUND

Gas-to-liquid (GTL) technology converts natural gas and other gaseous hydrocarbons into longer chain hydrocarbons such as gasoline and diesel fuel. Generally, the Fischer-Tropsch process provides the only commercially available GTL technology. However, Fischer-Tropsch plants have such a high capital cost that only 10 plants exist worldwide and none in the US.

A need has arisen for the development of small-scale, low capital expenditure, mini-plants for direct conversion of natural gas into high energy density liquid fuels at the place of extraction. Gas reserves in remote areas that do not have ready access to transportation facilities have the potential to ensure the economic and energy security of the US for the next several decades. In addition, converting natural gas to liquid would reduce the amount of natural gas 'flared' or burned off during the mining operations, approximately 12 billion cubic meters per year (E. A. Emam, Petroleum & Coal 57(5) 532, 2015). A typical small size plant for remote area operations may be as small as 100 L, i.e. orders of magnitude reduced size and capital costs when compared with the conventional Fischer Tropsch process.

Experimental catalysts such as transition metal doped zeolites have very low reactivity and poor selectivity, as they produce large amounts of undesired $CO_2$ (K. Narsimhan et al., ACS Cent. Sci., 2, 424, 2016). Because of their excellent methanol selectivity, method monooxygenase (MMO) enzymes would certainly be the ideal catalyst for methane oxidation. However, traditional enzymatic technologies have several disadvantages: they have very low volumetric methanol productivity (<0.05 g $CH_3OH/L_{reactor}$/hr) because they operate as diluted enzyme dispersions in water; have no mechanism for heat removal, which drastically reduce the catalyst lifetime; and low mass transfer rate to the aqueous phase due to very limited methane solubility in water (T. J. Lawton et al., J. Am. Chem. Soc., 138, 9327, 2016).

SUMMARY

According to aspects illustrated here, there is provided a catalyst having a porous support having at least one of thermally or electrically conductive particles bonded by a polymer, and enzymes embedded into pores of the porous support, and wherein the rate of the enzyme catalyzed reaction is higher than that of the free enzyme in the same conditions.

According to aspects illustrated here, there is provided a process of manufacturing an enzyme including forming a solution of monomers, enzymes, a solvent, and at least one of electrically and thermally conductive particles, polymerizing the monomers by adding initiators to the solution, and evaporating the solvent to produce an enzyme-embedded porous support catalyst.

According to aspects illustrated here, there is provided a process of manufacturing an enzyme embedded porous support, includes mixing enzymes, at least one of electrically conductive or thermally conductive particles, and a polymer in a solvent, and optionally evaporating the solvent.

DETAILED DESCRIPTION OF THE EMBODIMENTS

Figure 1:
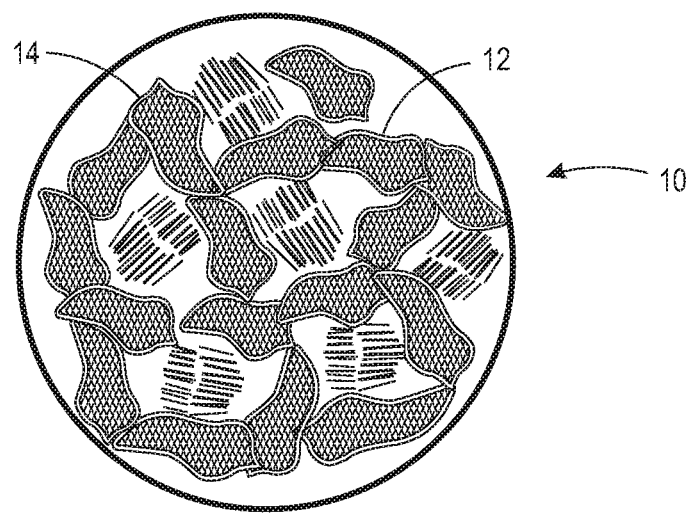
FIG. 1 shows an embodiment of an enzymatic catalyst.

The embodiments here involve a catalyst consisting of densely packed enzymes embedded in the pores of a thermally and/or electrically conductive porous support and wherein the rate of the enzyme catalyzed reaction is higher than that of the free enzyme in the same conditions.

In one embodiment, the thermally conductive catalyst is used with a gas or liquid cofactor, where the cofactor consists of an electron and proton source, in the presence of traces of water but in the absence of liquid water.

In another embodiment, the electrically conductive catalyst acts as an electrode in an electrochemical cell where the other electrode could be a conventional or a different type of enzymatic catalyst. The volume fraction occupied by the enzyme in the electrocatalyst is comprised in a range from 0.1% to 80%, the remaining volume fraction being occupied by the porous support and voids.

Regarding methane oxidation, the catalyst of the embodiments has unique features currently unavailable with the current state-of-the-art enzymatic methane oxidation catalytic reactors. These include dramatic increase of the enzyme loading achieved with compact engineered enzymes embedded into pores of high-capacity porous supports. Major mass transfer enhancements are achieved by allowing direct access of the methane and oxygen to the enzyme sites due to the elimination of water, a notoriously poor methane solvent. The embodiments also have increased enzyme/catalyst lifetime facilitated by rapid heat removal from the reaction sites by the thermally conductive porous support material and enzyme confinement to prevent denaturation.

In addition, other exothermal enzymatic processes, beside methane oxidation, are improved by the thermally controlled catalysts disclosed in the embodiments here. They encounter the same general problem, poor mass transfer due to poor solubility of the organic molecules in water.

One current solution fabricates enzymes embedded into nano-boehmite derived alumina ($Al_2O_3$) and has inherently good thermal conductivity similar to the embodiments here, as disclosed in V.V. Vinogradov, et al. *RSC Adv.*, 2015, 5 10862-10868. A conventional sol-gel process using an aluminum isopropoxide precursor. This differs from the embodiments disclosed here that use a bonding polymer binder and engineered particles with tailored size. Because there is no strong adhesion between the sol-gel particles, the bohemite support is too fragile to be usable for fabrication of a robust, pass-through catalytic membrane incorporating enzymes within the sol-gel matrix. More importantly, the process disclosed above is limited to only alumina or silica encapsulation, because those materials can be produced by sol-gel processes.

For example, the sol-gel approach described above cannot produce aerogels with non-sol-gel particles such as carbon, aluminum nitride, or silicon carbide, which have higher performance regarding electrical and thermal conductivity than alumina. In comparison, the embodiments disclosed here generally apply to any particles including thermally and conductive particles that cannot be produced by sol gel methods. Generally, suitable electrically conductive particles include carbon particles, carbon black, graphene, graphite, carbon nanotubes, and metal particles such as silver and copper particles or flakes. Suitable thermally conductive particles include aluminum nitrate, silicon carbide, aluminum nitride, boron arsenide, carbon nanotubes, graphene, graphite, and carbon nanoparticles and others.

FIG. 1 shows an embodiment of an enzymatic catalyst 10. The catalyst consists generally of an enzyme 14 contained within a network of thermally or electrically conductive particles 12. The thermally or electrically conductive particles may have any shape, including random, spherical, cylindrical, plate like shapes, fibers and other shapes.

Figure 2:
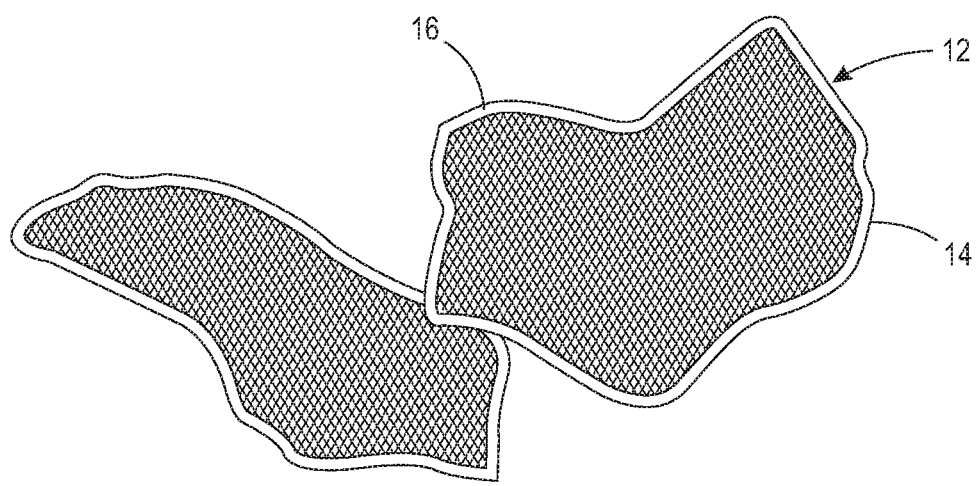
FIG. 2 shows an embodiment of an enzymatic catalyst particle.

FIG. 2 shows an embodiment of a thermally or electrically conductive particle 12. The thermally or electrically conductive material 18 has a thin layer of a polymer binder 16 that keeps the structural integrity of the porous support and as a result of the entire enzymatic catalyst 10 of FIG. 1.

Figure 3:
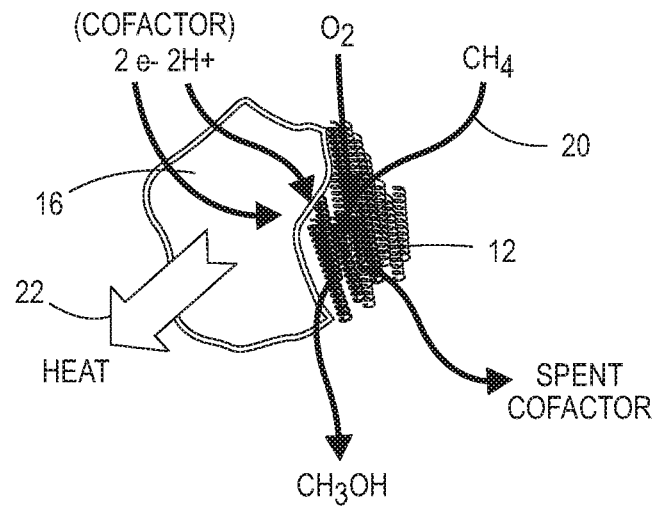
FIG. 3 shows an embodiment of a catalyst structure.

FIG. 3 shows illustrates the catalytic process for methane oxidation to methanol with the catalyst from FIG. 1. Methane 20, and the organic cofactor, which provides both electrons and protons react at the enzyme catalytic site 14 to produce methanol 26 and water as a by-product. The heat 22 generated by the reaction is removed rapidly by the thermally conductive particles 12 which encapsulate the enzyme and prevent the overheating of the enzyme overheating which would result in enzyme denaturation, or in other words loss of catalytic activity.

Figure 4:
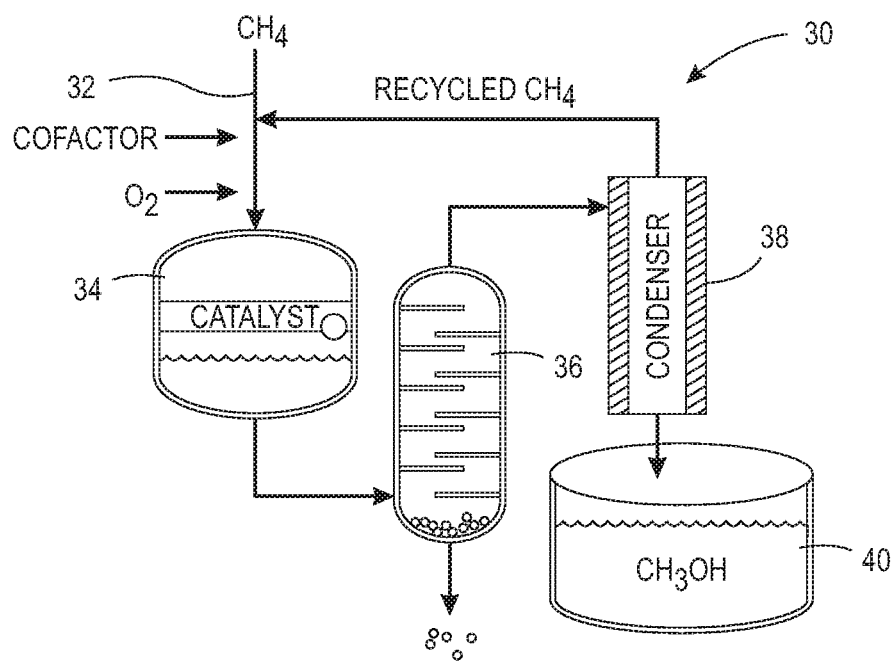
FIG. 4 shows a representation of an embodiment of a process for methane conversion.

FIG. 4 shows schematically an embodiment of a small scale mini plant for catalytic production of methanol from methane. Methane, cofactors and oxygen are fed to the catalyst consisting of MMO enzymes embedded into porous thermally conductive particles to produce methanol, water and spent cofactor in the reactor 34. The reaction mixture evacuated from the reactor 34 feeds into the separation column 36. Spent solid cofactor 35 is evacuated as a solid while heated mixture of methanol and water vapors are directed to condenser 38 to produce a mixture of ethanol and water. The final step is water removal from the methanol to produce dry methanol if required. This can be achieved for example by fractional distillation.

Generally speaking, in order to achieve high thermal and/or electrical conduction, the concentration of the thermally or electrically conductive particles has to be sufficient so that they reach a percolation threshold so that particles are in contact with their neighboring particles. The actual amount of particles required to achieve the percolation level is dependent, to some level on the shape of the particles. For example, particles with a longer aspect ratio will have a lower percolation threshold when compared with for example spherical particles.

The embodiments disclosed here may use organic cofactors in a gas phase, such as methane monooxygenase (MMO). Traditional MMO bioreactors require water for solubilization and transportation of the nicotinamide adenine dinucleotide (NADH) cofactor, the source of electrons and protons, to the active sites of the enzyme, acting as a reducing agent. The enzymatic catalysis could work efficiently in the absence of liquid water if the cofactors can access the enzyme sites directly without the need of the solvent. They could be gases or liquids.

FIG. 3 shows an embodiment of an enzymatic catalyst that uses MMO as a cofactor in the conversion of methane gas ($CH_4$) 20 to methyl alcohol, methanol, ($CH_3OH$) 26. The methane passes through the enzymatic catalyst 10 with oxygen 28 and the cofactor 24, to produce heat 22, methanol 26, and the spent cofactor 29. While this particular embodiment shows the use of MMO, one should not that any organic cofactor could be used.

A range of such reducing agents have been identified that are liquid at room temperatures. Molecules with low boiling points, such as tetramethyldisiolane (TDSMO) with a boiling point of 70° C., enable an all gas-phase process at low temperatures (<100° C.). All-gas processes allow easy access of the reagents ($CH_4$ and $O_2$) and co-factors to enzymes through the aerogel process. As an added benefit, elimination of the expensive and temperature-sensitive NADH decreases process costs. A potential challenge of this proposed process arises in the removal of the spent cofactor, which is the oxidized form of the cofactor after reaction. Generally, the oxidized forms of organic reducing agents are organic salts that have good solubility in the produced methanol and can separate from the solution by a simple distillation.

Suitable reducing agents, that are either liquids or solids at room temperature but could operate in gas or liquid phase if allowed to heat at temperatures above their melting or boiling point include:

| Reducing Agent | Physical State at Room Temp (25° C.) | Melting Point (° C.) | Boiling Point (° C.) |
| --- | --- | --- | --- |
| Trimethlyphosphine | Liquid | N/A | 40 |
| Tetramethyldisiloxane | Liquid | N/A | 70 |
| Methyldiethoxysilane | Liquid | N/A | 95 |
| Dithiothreitol | Solid | 42 | 130 |
| Triphenylphosphite | Liquid | 24 | 360 |
| 3-Mercaptopropionic | Liquid | N/A | 110 (vac) |

The reactivity and stability of enzymes in the presence of organic molecules and at temperatures higher than ambient conditions present challenges for these embodiments. The aerogel has two main roles in achieving the proposed performance. First, it confines the enzyme within the pores to prevent denaturation. Encapsulation enhances thermal stability and reactivity as well as stability in the presence of organic solvents. Both physical immobilization and increased enzyme structure rigidity in organic solvents prevent conformational changes responsible for enzyme deactivation. This is beneficial because it enables to perform the catalytic reactions at a wider range than usually available with unencapsulated enzymes, which quickly denature when heated above 40-50° C. The catalyst from the present invention is suitable for reaction temperatures from about 1° C. to about 150° C. Reaction at higher temperatures increases the reaction rate and therefore the throughput of the enzyme catalyzed process.

The encapsulation also increases the stability of the enzymes in higher than ambient pressure. Reactions can be performed at pressures in a range from 1 atmosphere to 20 atmospheres. High pressure is beneficial because it accelerates the reaction rate.

Additionally, the porous support has high thermal conductivity. The lack of stirring and large volume of solution may result in a quickly rising temperature of the membrane catalysts in turn decreasing the enzyme activity. Highly thermally conductive porous support materials remains crucial for the removal of the localized heat associated with high methanol production rates.

The fabrication process consists of direct incorporation and immobilization of MMO, or other cofactor, enzymes into an aerogel or other porous support precursor material, followed by curing and solvent evaporation. The pores within the porous support result from free space between particles after solvent evaporation. Solvent evaporation is an optional step. For example, if the solvent used for fabrication of the porous support is suitable for the catalytic process, then solvent may not need to be evaporated before use of the catalyst.

FIG. 4 shows an embodiment of a process of using an enzymatic catalyst to convert methane gas to liquid methanol. The methane gas 20, along with oxygen and a cofactor, if used, enter a reactor chamber 34. The reaction mixture from 34 feeds into the separation chamber 36. If the mixture is not already hot, it may be heated. Solid spent cofactor material and water may accumulate at the bottom of the separation chamber 36. Water has a higher boiling point than methanol, so will accumulate with the solids. These waste products are then removed as needed. The gaseous mixture is then condensed at condenser 38 to produce liquid methanol 26, an easily transportable liquid result from the gas to liquid process.

In one embodiment, the enzyme-embedded porous support results from polymerization of monomers and initiators in the presence of either electrically or thermally conductive particles, or both, in water solvent, and at temperatures that are close to the ambient temperatures, defined here as less than 50° C. An advantage of this process lies in its production of a cross-linked conductive porous support that operates in water as required, for example, in an electrochemical cell.

Examples of monomers include vinyl, acrylate, and methacrylate monomers. Examples of suitable acrylates and methacrylates include (a) monofunctional acrylates and methacrylates such as methyl acrylate, ethyl acrylate, methyl methacrylate, ethyl methacrylate, benzyl methacrylate, lauryl methacrylate, isobornyl methacrylate (b) difunctional acrylates and methacrylates such as 1,3-butanediol diacrylate, 1,6-hexanediol diacrylate, bisphenol A ethoxylate diacrylate, ethylene glycol diacrylate, poly(ethylene glycol) diacrylate, (c) tri, tetra, penta or hexa-acrylates and methacrylates such as trimethylolpropane triacrylate, trimethylolpropane ethoxylate triacrylate, di(trimethylolpropane) tetraacrylate, dipentaerythritol penta-/hexa-acrylate and the like. Suitable vinyl monomers include styrene, divinylbenzene and liquid ethylene derivatives such as, vinyl stearate, vinyl laurate, vinyl benzoate, vinyl acetate, ethyl vinyl ether, vinyl chloride, 1-vinyl-2-pyrrolidone.

Examples of radical initiators include thermal initiators—activated by heat—and photoinitiators which are activated by light, typically Ultra Violet in a range of about 200 nm to 400 nm wavelength. Non-limiting examples of thermal initiators includes (a) peroxides such as benzoyl peroxide, diacetylperoxide, di t-butylperoxide, cumyl peroxide; or azo compounds such as AIBN and Phenylazotriphenylmethane. Non-limiting examples of photoinitiators include benzophenone, benzyl, benzoin and the like. In addition to water, other solvents may include mixtures of water with other compatible solvents, such as ethanol, propanol or butanol. The ratio of the other solvent to water may range from 0.1:99.9 to 90:10.

In another embodiment, the enzyme-embedded porous support results from mixing particles and enzymes in water with a small amount of polymer, followed by optional solvent evaporation. This process creates a structure in which the polymer glue in the porous structure holds the particles together. The amount of polymer is generally chosen such as that on drying to form a thin layer of dry polymer after evaporation that will act as a binder to keep the particles together and maintain the structural integrity of the enzyme/particle catalyst. Suitable polymers are those that are soluble in water or mixtures of water with other solvents. Examples of suitable polymers include polyvinylpyrrolidone, polyvinyl alcohol, polyethylene glycols, polyacrylamides, polyethyleneoxide, poly 2-hydroxyethyl methacrylate, and hydroxypropyl methylcellulose.

Copolymers made of more hydrophobic polymers and hydrophilic polymer segments are also suitable for this invention. Some examples include poly(acrylic acid-co-styrene), acetate-ethylene copolymer, ethylene vinyl acetate, polyethylene glycol—polycaprolactone, and polyethylene glycol—polyethyleneimine. This may result in incorporation of large amounts of particles into the polymer, giving it a high particle to polymer ratio. The amount of polymer with respect to the amount of particles is small. The weight/weight ratio between the polymer and particles is comprised in a range from 0.1 to 50%. This makes the porous support structure particularly suited for processes that take place in the absence of water, or that use only small amounts of water, and where fast heat removal is required. This embodiment uses a high content of thermally conductive particles.

Thermally conductive particles may include $Al_2O_3$, having a thermal conductivity of 32 W/m·K, SiC having a thermally conductivity of 60 W/m·K, and AlN having a thermal conductivity of 150 W/m·K. Other thermally conductive particles include boron arsenide, carbon nanotubes, graphene, graphite, and carbon nanoparticles. Electrically conductive particles may include carbon nanoparticles, carbon black, activated carbon particles, and silver and copper particles or flakes.

The embodiments above discuss the use of MMO (methane monooxygenase) for methane oxidation. However, other potential process to which the proposed enzyme-embedded porous support may apply may require different substrates and enzymes. Example alternative applicable enzymatic processes include, but are not limited to: proteinases, protein-catabolic enzymes which hydrolyze peptide bonds, applicable to food and pharmaceutical industries; xylanase, involved in the depolymerization of xylan, a hemicellulose, and finds applications in bleaching pulp paper, extraction of oils from plants; and lipase, capable of breaking down lipids, having application in the conversion of oil into fuel. The enzymes may consist of natural enzymes, such as these, or could be engineered, meaning that they result from genetic modifications.

In this manner, a dramatic increase of enzyme loading into pores of high-capacity porous supports compared to the concentration achievable in aqueous solutions. Additionally, major mass transfer enhancement occurs by allowing direct access of the organic substrates, such as methane, to the enzyme sites due to the elimination of water, a notoriously bad solvent for organic molecules. The embodiments also achieve higher potential reactor operating temperatures and increased enzyme lifetime facilitated by better thermal control of the reaction sites by thermally conductive porous support materials and enzyme confinement to prevent denaturation.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A catalyst, comprising:
    a polymer porous support including at least one of thermally or electrically conductive particles coated with a layer of the polymer and bonded to the polymer porous support; and
    enzymes embedded into pores of the polymer porous support to produce embedded enzymes,
    wherein a lifetime of the embedded enzymes is longer than a lifetime of the enzymes not embedded into the pores in the same conditions.

2. The catalyst of claim 1, wherein the particles comprise thermally conductive particles of at least one selected from the group consisting of: aluminum oxide; silicon carbide; aluminum nitride; boron arsenide; carbon nanotubes; graphene; graphite; and carbon nanoparticles.

3. The catalyst of claim 1, wherein the particles comprise electrically conductive particles of at least one selected from the group consisting of: carbon nanoparticles; graphene; graphite; carbon nanotubes; carbon black; silver and copper particles or flakes.

4. The catalyst of claim 1, wherein the particles have a size in a range of 1 nanometer to 500 nanometers.

5. The catalyst of claim 1, wherein the catalyst forms an electrode in an electrochemical cell.

6. The catalyst of claim 5, wherein a volume fraction occupied by the embedded enzymes in the catalyst is in a range from 0.1% to 80%, a remaining volume fraction being occupied by the porous support and voids of empty space.

7. The catalyst of claim 1, wherein the particles are thermally conductive particles and are selected from the group consisting of: aluminum nitrate; silicon carbide; aluminum nitride; boron arsenide; carbon nanotubes; graphene; graphite; and carbon nanoparticles.

8. The catalyst of claim 1, wherein the particles are electrically conductive particles and are selected from the group consisting of: carbon particles; carbon black; graphene; graphite; carbon nanotubes; and metal particles or flakes.

9. The catalyst of claim 1, wherein the electrically or thermally conductive particles have a shape of one of random; spherical; cylindrical; plate like shapes; and fibers.

10. The catalyst of claim 1, wherein the enzymes embedded into pores of the porous support include at least one selected from the group consisting of: methane monooxygenase; proteinases; protein-catabolic enzymes; xylanase; and lipase.

11. The catalyst of claim 1, wherein the enzymes are at least one of natural enzymes, or engineered enzymes.

12. The catalyst of claim 1, wherein the polymer is a result of polymerization of monomers selected from the group consisting of: monofunctional acrylates and methacrylates; difunctional acrylates and methacrylates; tri, tetra, penta or hexa-acrylates and methacrylates; styrene; divinylbenzene; vinyl stearate; vinyl laurate; vinyl benzoate; vinyl acetate; ethyl vinyl ether; vinyl chloride; and 1-vinyl-2-pyrrolidone.

13. The catalyst of claim 1, wherein the polymer is a water soluble polymer.

14. The catalyst of claim 1, wherein the polymer is selected from a group consisting of polyvinylpyrrolidone; polyvinyl alcohol; polyethylene glycols; polyacrylamides; polyethyleneoxide; poly 2-hydroxyethyl methacrylate; and hydroxypropyl methylcellulose.

15. The catalyst of claim 1, wherein a weight to weight ratio between the polymer and particles is in a range from 0.1 to 50%.

16. The catalyst of claim 1, wherein a thermal conductivity of the particles is greater than or equal to 32 W/m·K.

17. The catalyst of claim 10, wherein the enzymes comprise
    methane monooxygenase enzymes.

18. The catalyst of claim 17, wherein the methane monooxygenase enzymes are one of either natural methane monooxygenase enzymes or engineered methane monooxygenase enzymes.

19. The catalyst of claim 17, wherein a thermal conductivity of the particles is greater than or equal to 32 W/m·K.

20. The catalyst of claim 17, wherein a volume fraction occupied by the embedded methane monooxygenase enzymes in the catalyst is in a range from 0.1% to 80%, and a remaining volume fraction being occupied by the porous support and voids of empty space.

* * * * *